(12) United States Patent
Coggins et al.

(10) Patent No.: US 8,568,160 B2
(45) Date of Patent: Oct. 29, 2013

(54) ECG ADAPTER SYSTEM AND METHOD

(75) Inventors: Scott R. Coggins, Littleton, MA (US); Mark J. Callahan, Medway, MA (US); Steven A. Holley, Cumming, GA (US); Dimitrios J. Theodorou, Franklin, MA (US)

(73) Assignee: Covidien LP, Mansfield, MA (US)

( * ) Notice: Subject to any disclaimer, the term of this patent is extended or adjusted under 35 U.S.C. 154(b) by 98 days.

(21) Appl. No.: 13/192,022

(22) Filed: Jul. 27, 2011

(65) Prior Publication Data

US 2012/0028504 A1 Feb. 2, 2012

Related U.S. Application Data

(60) Provisional application No. 61/368,730, filed on Jul. 29, 2010.

(51) Int. Cl.
*H01R 11/00* (2006.01)
(52) U.S. Cl.
USPC .......................................... 439/502; 600/393
(58) Field of Classification Search
USPC ................. 600/372, 373, 386, 393, 508, 509; 439/502–506, 623, 628, 909
See application file for complete search history.

(56) References Cited

U.S. PATENT DOCUMENTS

| | | |
|---|---|---|
| 3,606,881 A | 9/1971 | Woodson |
| 3,752,151 A | 8/1973 | Robichaud |
| 3,805,769 A | 4/1974 | Sessions |
| 3,828,766 A | 8/1974 | Krasnow |
| 3,868,946 A | 3/1975 | Hurley |
| 3,888,240 A | 6/1975 | Reinhold, Jr. et al. |
| 3,895,635 A | 7/1975 | Justus et al. |
| 3,901,218 A | 8/1975 | Buchalter |
| 3,998,213 A | 12/1976 | Price |
| 4,027,664 A | 6/1977 | Heavner, Jr. et al. |
| 4,034,854 A | 7/1977 | Bevilacqua |
| 4,077,397 A | 3/1978 | Ellis et al. |
| 4,112,941 A | 9/1978 | Larimore |
| 4,166,465 A | 9/1979 | Esty et al. |

(Continued)

FOREIGN PATENT DOCUMENTS

| | | |
|---|---|---|
| DE | 90 02 539 U1 | 5/1990 |
| DE | 10 2004 032 410 A1 | 1/2006 |

(Continued)

OTHER PUBLICATIONS

European Office Action dated Dec. 20, 2011 for European Patent Appln. No. EP 07 253 850.7.

(Continued)

*Primary Examiner* — Thanh Tam Le
(74) *Attorney, Agent, or Firm* — Lisa E. Winsor, Esq.

(57) ABSTRACT

An electrocardiograph (ECG) adapter including an adapter body having a first end and a second end is presented. A monitor connector is positioned at the first end of the adapter body, the monitor connector adapted for coupling to an input of an ECG monitor. A first lead receptacle is positioned at the second end of the adapter body, the first lead receptacle configured to receive a first connector having a first pin configuration. A second lead receptacle is positioned at the second end of the adapter body, the second lead receptacle located adjacent the first lead receptacle and configured to receive a second connector having a second pin configuration different from the first pin configuration.

12 Claims, 7 Drawing Sheets

(56) References Cited

U.S. PATENT DOCUMENTS

| | | | |
|---|---|---|---|
| 4,353,372 A | 10/1982 | Ayer | |
| 4,365,634 A | 12/1982 | Bare et al. | |
| 4,477,801 A * | 10/1984 | Robinson et al. ............. 340/684 |
| 4,498,480 A | 2/1985 | Mortensen | |
| 4,729,377 A | 3/1988 | Granek et al. | |
| 4,763,660 A | 8/1988 | Kroll et al. | |
| 4,781,200 A | 11/1988 | Baker | |
| 4,785,822 A | 11/1988 | Wallace | |
| 4,815,964 A | 3/1989 | Cohen et al. | |
| 4,909,260 A | 3/1990 | Salem et al. | |
| 4,947,846 A | 8/1990 | Kitagawa et al. | |
| 4,957,109 A | 9/1990 | Groeger et al. | |
| 5,080,604 A | 1/1992 | Rider et al. | |
| 5,083,238 A | 1/1992 | Bousman | |
| 5,083,933 A | 1/1992 | Colleran et al. | |
| 5,104,253 A | 4/1992 | Zielinski et al. | |
| 5,104,334 A | 4/1992 | Honma et al. | |
| 5,131,854 A | 7/1992 | Jose et al. | |
| 5,137,466 A | 8/1992 | Endo et al. | |
| 5,154,646 A | 10/1992 | Shoup | |
| 5,158,469 A | 10/1992 | Martin | |
| 5,160,276 A | 11/1992 | Marsh et al. | |
| 5,173,059 A | 12/1992 | Sato et al. | |
| 5,176,343 A | 1/1993 | Cheney, II et al. | |
| 5,178,556 A | 1/1993 | Chen | |
| 5,180,312 A | 1/1993 | Martin | |
| 5,190,467 A | 3/1993 | Ohta | |
| 5,192,226 A | 3/1993 | Wang | |
| 5,197,901 A | 3/1993 | Hashiguchi | |
| 5,199,897 A | 4/1993 | Hashiguchi | |
| 5,201,669 A | 4/1993 | Lin | |
| 5,203,715 A | 4/1993 | Yamamoto | |
| 5,203,719 A | 4/1993 | Kozono | |
| 5,232,383 A | 8/1993 | Barnick | |
| 5,234,357 A | 8/1993 | Yamaguchi | |
| 5,243,510 A | 9/1993 | Cheney, II | |
| 5,263,481 A | 11/1993 | Axelgaard | |
| 5,276,443 A | 1/1994 | Gates et al. | |
| 5,278,759 A | 1/1994 | Berra et al. | |
| 5,293,013 A | 3/1994 | Takahashi | |
| 5,320,621 A | 6/1994 | Gordon et al. | |
| 5,326,272 A | 7/1994 | Harhen et al. | |
| 5,332,330 A | 7/1994 | Kaneko | |
| 5,338,219 A | 8/1994 | Hiramoto | |
| 5,341,806 A | 8/1994 | Gadsby et al. | |
| 5,341,812 A | 8/1994 | Allaire et al. | |
| 5,353,793 A | 10/1994 | Bornn | |
| 5,362,249 A | 11/1994 | Carter | |
| 5,370,116 A | 12/1994 | Rollman et al. | |
| 5,370,550 A | 12/1994 | Alwine et al. | |
| 5,376,016 A | 12/1994 | Inaba et al. | |
| 5,378,168 A | 1/1995 | Sumida | |
| 5,380,223 A | 1/1995 | Marsh et al. | |
| 5,382,176 A | 1/1995 | Norden | |
| 5,383,794 A | 1/1995 | Davis et al. | |
| 5,387,116 A | 2/1995 | Wang | |
| 5,387,127 A | 2/1995 | Wang | |
| 5,399,045 A | 3/1995 | Yoneda et al. | |
| 5,405,269 A | 4/1995 | Stupecky | |
| 5,415,164 A | 5/1995 | Faupel et al. | |
| 5,429,526 A | 7/1995 | Ann | |
| 5,454,739 A | 10/1995 | Strand | |
| 5,462,448 A | 10/1995 | Kida et al. | |
| 5,486,117 A | 1/1996 | Chang | |
| 5,507,290 A | 4/1996 | Kelly et al. | |
| 5,507,665 A | 4/1996 | Oda | |
| 5,507,668 A | 4/1996 | Lambrinos et al. | |
| 5,509,822 A | 4/1996 | Negus et al. | |
| 5,511,553 A | 4/1996 | Segalowitz | |
| 5,546,950 A | 8/1996 | Schoeckert et al. | |
| 5,558,535 A | 9/1996 | Saka et al. | |
| 5,564,939 A | 10/1996 | Maitani et al. | |
| 5,582,180 A | 12/1996 | Manset et al. | |
| 5,584,719 A | 12/1996 | Tsuji et al. | |
| 5,599,199 A | 2/1997 | Wright | |
| 5,603,632 A | 2/1997 | Johannes et al. | |
| 5,611,708 A | 3/1997 | Mizunuma et al. | |
| 5,613,870 A | 3/1997 | Traver, Jr. | |
| 5,615,674 A | 4/1997 | Maurer | |
| 5,622,168 A | 4/1997 | Keusch et al. | |
| 5,624,271 A | 4/1997 | Childs et al. | |
| 5,626,135 A | 5/1997 | Sanfilippo | |
| 5,632,274 A | 5/1997 | Quedens et al. | |
| 5,651,689 A | 7/1997 | Plyler et al. | |
| 5,653,606 A | 8/1997 | Chrysostomou | |
| 5,674,088 A | 10/1997 | Roche et al. | |
| 5,676,694 A | 10/1997 | Boser et al. | |
| 5,679,022 A | 10/1997 | Cappa | |
| 5,679,029 A | 10/1997 | Saunier et al. | |
| 5,685,303 A | 11/1997 | Rollman et al. | |
| 5,695,355 A | 12/1997 | Hasenfratz et al. | |
| 5,702,265 A | 12/1997 | Yamaguchi | |
| 5,704,351 A | 1/1998 | Mortara et al. | |
| 5,711,684 A | 1/1998 | Inoue et al. | |
| 5,718,596 A | 2/1998 | Inaba et al. | |
| 5,724,025 A | 3/1998 | Tavori | |
| 5,724,984 A | 3/1998 | Arnold et al. | |
| 5,725,525 A | 3/1998 | Kordis | |
| 5,741,155 A | 4/1998 | Herman | |
| 5,749,746 A | 5/1998 | Tan et al. | |
| 5,769,650 A | 6/1998 | Aoyama et al. | |
| 5,772,591 A | 6/1998 | Cram | |
| 5,775,953 A | 7/1998 | Yamanashi et al. | |
| 5,782,647 A | 7/1998 | Okura et al. | |
| 5,782,892 A | 7/1998 | Castle et al. | |
| 5,788,527 A | 8/1998 | Sanders et al. | |
| 5,797,854 A | 8/1998 | Hedgecock | |
| 5,806,152 A | 9/1998 | Saitou et al. | |
| 5,813,404 A | 9/1998 | Devlin et al. | |
| 5,813,979 A | 9/1998 | Wolfer | |
| 5,827,086 A | 10/1998 | Fukuda | |
| 5,830,000 A | 11/1998 | Shifflett et al. | |
| 5,836,783 A | 11/1998 | Morisawa et al. | |
| 5,843,141 A | 12/1998 | Bischoff et al. | |
| 5,848,456 A | 12/1998 | Sjoqvist | |
| 5,865,740 A | 2/1999 | Kelly et al. | |
| 5,865,741 A | 2/1999 | Kelly et al. | |
| 5,871,451 A | 2/1999 | Unger et al. | |
| 5,873,747 A | 2/1999 | Tsuji | |
| 5,876,232 A | 3/1999 | Matsushita et al. | |
| 5,895,284 A | 4/1999 | Kocher et al. | |
| 5,904,579 A | 5/1999 | McLean et al. | |
| 5,913,834 A | 6/1999 | Francais | |
| 5,916,159 A | 6/1999 | Kelly et al. | |
| 5,931,689 A | 8/1999 | Patel | |
| 5,931,861 A | 8/1999 | Werner et al. | |
| 5,934,926 A | 8/1999 | Gabrisko, Jr. et al. | |
| 5,937,950 A | 8/1999 | Adams et al. | |
| 5,938,470 A | 8/1999 | Kashiyama | |
| 5,938,597 A | 8/1999 | Stratbucker | |
| 5,941,725 A | 8/1999 | Brennan et al. | |
| 5,951,316 A | 9/1999 | Kawano et al. | |
| 5,964,624 A | 10/1999 | Pernelle | |
| 5,968,087 A | 10/1999 | Hess et al. | |
| 5,971,790 A | 10/1999 | Rohde | |
| 5,971,799 A | 10/1999 | Swade | |
| 5,980,332 A | 11/1999 | Tsuji et al. | |
| 5,984,717 A | 11/1999 | Lee | |
| 5,997,334 A | 12/1999 | Goto | |
| 6,006,125 A | 12/1999 | Kelly et al. | |
| 6,027,359 A | 2/2000 | Aoki et al. | |
| 6,032,063 A | 2/2000 | Hoar et al. | |
| 6,032,064 A | 2/2000 | Devlin et al. | |
| 6,036,533 A * | 3/2000 | Huang ......................... 439/502 |
| 6,038,479 A | 3/2000 | Werner et al. | |
| 6,038,481 A | 3/2000 | Werner et al. | |
| 6,050,838 A | 4/2000 | Norizuki et al. | |
| 6,055,448 A | 4/2000 | Anderson et al. | |
| 6,062,902 A | 5/2000 | Buckles et al. | |
| 6,066,093 A | 5/2000 | Kelly et al. | |
| 6,074,234 A | 6/2000 | Hasegawa | |
| 6,098,127 A | 8/2000 | Kwang | |
| 6,109,948 A | 8/2000 | Kuo | |
| 6,115,623 A | 9/2000 | McFee | |

(56) References Cited

U.S. PATENT DOCUMENTS

| | | | |
|---|---|---|---|
| 6,116,940 A | 9/2000 | Bertens et al. | |
| 6,122,536 A | 9/2000 | Sun et al. | |
| 6,122,544 A | 9/2000 | Organ | |
| 6,129,666 A | 10/2000 | DeLuca et al. | |
| 6,132,233 A | 10/2000 | Fukuda | |
| 6,139,350 A | 10/2000 | Mathesius | |
| 6,139,360 A | 10/2000 | Hayashi | |
| 6,152,778 A | 11/2000 | Dalton | |
| 6,155,864 A | 12/2000 | Yoshiura | |
| 6,157,851 A | 12/2000 | Kelly et al. | |
| 6,165,017 A | 12/2000 | Kuo | |
| 6,168,453 B1 | 1/2001 | Kuo | |
| 6,171,139 B1 | 1/2001 | Sato et al. | |
| 6,177,673 B1 * | 1/2001 | Blomberg et al. | 250/339.01 |
| 6,190,385 B1 | 2/2001 | Tom et al. | |
| 6,203,354 B1 | 3/2001 | Kuwahara et al. | |
| 6,219,568 B1 | 4/2001 | Kelly et al. | |
| 6,219,569 B1 | 4/2001 | Kelly et al. | |
| 6,223,088 B1 | 4/2001 | Scharnberg et al. | |
| 6,232,366 B1 | 5/2001 | Wang et al. | |
| 6,234,827 B1 | 5/2001 | Nishio et al. | |
| 6,236,874 B1 | 5/2001 | Devlin et al. | |
| 6,240,323 B1 | 5/2001 | Calenzo, Sr. et al. | |
| 6,247,963 B1 | 6/2001 | Rattner | |
| 6,250,955 B1 | 6/2001 | Archuleta | |
| 6,254,425 B1 | 7/2001 | Shchervinsky et al. | |
| 6,257,914 B1 | 7/2001 | Comerci et al. | |
| 6,257,925 B1 | 7/2001 | Jones | |
| 6,280,209 B1 | 8/2001 | Bassler et al. | |
| 6,280,227 B1 | 8/2001 | Terada et al. | |
| 6,280,243 B1 | 8/2001 | Liu et al. | |
| 6,283,789 B1 | 9/2001 | Tsai | |
| 6,290,530 B1 | 9/2001 | Chang | |
| 6,298,255 B1 | 10/2001 | Cordero et al. | |
| 6,304,783 B1 | 10/2001 | Lyster et al. | |
| 6,324,432 B1 | 11/2001 | Rigaux et al. | |
| 6,339,720 B1 | 1/2002 | Anzellini et al. | |
| 6,340,306 B1 | 1/2002 | Daoud | |
| 6,356,779 B1 | 3/2002 | Katzenmaier et al. | |
| 6,358,083 B1 | 3/2002 | Kraft | |
| 6,360,119 B1 | 3/2002 | Roberts | |
| 6,364,685 B1 | 4/2002 | Manning | |
| 6,383,010 B1 | 5/2002 | Mayo et al. | |
| 6,383,011 B2 | 5/2002 | Chen | |
| 6,383,036 B1 | 5/2002 | Steinhauser et al. | |
| 6,386,917 B1 | 5/2002 | Sakaguchi | |
| 6,393,317 B1 | 5/2002 | Fukuda et al. | |
| 6,394,953 B1 | 5/2002 | Devlin et al. | |
| 6,398,575 B1 | 6/2002 | Bresson | |
| 6,398,577 B1 | 6/2002 | Simmel et al. | |
| 6,400,977 B1 | 6/2002 | Kelly et al. | |
| 6,411,834 B1 | 6/2002 | Nagai | |
| 6,413,112 B2 | 7/2002 | Semmeling et al. | |
| 6,415,169 B1 | 7/2002 | Kornrumpf et al. | |
| 6,419,636 B1 | 7/2002 | Young et al. | |
| 6,434,410 B1 | 8/2002 | Cordero et al. | |
| 6,447,170 B1 | 9/2002 | Takahashi et al. | |
| 6,453,186 B1 | 9/2002 | Lovejoy et al. | |
| 6,454,577 B1 | 9/2002 | Yi | |
| 6,454,590 B1 | 9/2002 | Goodrich et al. | |
| 6,454,605 B1 | 9/2002 | Bassler et al. | |
| 6,456,872 B1 | 9/2002 | Faisandier | |
| 6,461,179 B1 | 10/2002 | Sullivan et al. | |
| 6,487,430 B1 | 11/2002 | Henderson et al. | |
| 6,494,744 B1 | 12/2002 | Lee | |
| 6,514,099 B2 | 2/2003 | Endo | |
| 6,517,372 B1 | 2/2003 | Jones | |
| 6,531,657 B1 | 3/2003 | Jones, Jr. et al. | |
| 6,533,600 B1 | 3/2003 | Kashiyama et al. | |
| 6,540,549 B2 | 4/2003 | Rupert | |
| 6,551,117 B2 | 4/2003 | Poplawski et al. | |
| 6,553,246 B1 | 4/2003 | Wenger | |
| 6,553,250 B2 | 4/2003 | Rantala | |
| 6,558,189 B1 | 5/2003 | Groebe et al. | |
| 6,561,834 B2 | 5/2003 | Chen | |
| 6,564,079 B1 | 5/2003 | Cory et al. | |
| 6,565,388 B1 | 5/2003 | Van Woensel et al. | |
| 6,567,680 B2 | 5/2003 | Swetlik et al. | |
| 6,575,759 B1 | 6/2003 | Ollivier | |
| 6,575,794 B1 | 6/2003 | Nakamura | |
| 6,582,252 B1 | 6/2003 | Lin | |
| 6,589,066 B1 | 7/2003 | Wu | |
| 6,592,391 B1 | 7/2003 | Wu | |
| 6,592,404 B2 | 7/2003 | Endo | |
| 6,604,963 B2 | 8/2003 | Lin | |
| 6,607,397 B1 | 8/2003 | Zhang et al. | |
| 6,609,018 B2 | 8/2003 | Cory et al. | |
| 6,609,833 B1 | 8/2003 | Miyachi et al. | |
| 6,611,705 B2 | 8/2003 | Hopman et al. | |
| 6,612,860 B2 | 9/2003 | Droesbeke | |
| 6,619,976 B2 | 9/2003 | Huetter et al. | |
| 6,619,989 B1 | 9/2003 | Yi | |
| 6,623,312 B2 | 9/2003 | Merry et al. | |
| 6,636,754 B1 | 10/2003 | Baura et al. | |
| 6,647,286 B1 | 11/2003 | Kato et al. | |
| 6,648,665 B1 | 11/2003 | Wu | |
| 6,648,666 B1 | 11/2003 | Wu | |
| 6,654,626 B2 | 11/2003 | Devlin et al. | |
| 6,655,979 B1 | 12/2003 | Lee | |
| 6,659,790 B1 | 12/2003 | Wi | |
| 6,663,412 B2 | 12/2003 | Aramoto et al. | |
| 6,663,419 B2 | 12/2003 | Vaden | |
| 6,663,420 B1 | 12/2003 | Xiao | |
| 6,663,570 B2 | 12/2003 | Mott et al. | |
| 6,669,510 B2 | 12/2003 | Yamawaki et al. | |
| 6,688,894 B2 | 2/2004 | Knox, Jr. et al. | |
| 6,688,907 B2 | 2/2004 | Yamaoka et al. | |
| 6,702,602 B2 | 3/2004 | Wu | |
| 6,702,603 B2 | 3/2004 | Wu | |
| 6,702,616 B1 | 3/2004 | Chang et al. | |
| 6,705,880 B2 * | 3/2004 | Rhude | 439/144 |
| 6,709,284 B1 | 3/2004 | Avlonitis | |
| 6,716,165 B1 * | 4/2004 | Flanders et al. | 600/301 |
| 6,722,912 B2 | 4/2004 | Wu | |
| 6,736,650 B1 | 5/2004 | Chen | |
| 6,743,053 B2 | 6/2004 | Wu | |
| 6,748,797 B2 | 6/2004 | Breed et al. | |
| 6,751,493 B2 | 6/2004 | Wenger | |
| 6,755,689 B2 | 6/2004 | Zhang et al. | |
| 6,768,921 B2 | 7/2004 | Organ et al. | |
| 6,773,293 B1 | 8/2004 | Lee | |
| 6,780,065 B2 | 8/2004 | Schwarz | |
| 6,786,755 B2 | 9/2004 | Dambach et al. | |
| 6,786,764 B2 | 9/2004 | Sivertsen | |
| 6,805,579 B2 * | 10/2004 | Marchand et al. | 439/502 |
| 6,816,744 B2 | 11/2004 | Garfield et al. | |
| 6,832,928 B2 | 12/2004 | Suzuki | |
| 6,837,734 B2 | 1/2005 | Ushio et al. | |
| 6,847,836 B1 | 1/2005 | Sujdak | |
| 6,848,926 B2 | 2/2005 | Ling et al. | |
| 6,851,969 B2 | 2/2005 | Archuletta | |
| 6,860,750 B1 | 3/2005 | Wu | |
| 6,866,535 B2 | 3/2005 | Uchida | |
| 6,881,098 B2 | 4/2005 | Jeansonne et al. | |
| 6,891,379 B2 | 5/2005 | Kelly et al. | |
| 6,913,482 B1 | 7/2005 | Wu | |
| 6,939,158 B2 | 9/2005 | Moffett et al. | |
| 6,939,345 B2 | 9/2005 | KenKnight et al. | |
| 6,945,796 B2 | 9/2005 | Bassler et al. | |
| 6,945,807 B1 | 9/2005 | Wu | |
| 6,948,973 B1 | 9/2005 | Hsu et al. | |
| 6,970,731 B1 | 11/2005 | Jayaraman et al. | |
| 6,973,341 B2 | 12/2005 | Watson | |
| 6,973,343 B2 | 12/2005 | Wenger | |
| 6,980,852 B2 | 12/2005 | Jersey-Willuhn et al. | |
| 6,984,143 B2 | 1/2006 | Roese | |
| 6,997,733 B2 | 2/2006 | Peng | |
| 7,004,787 B2 | 2/2006 | Milan | |
| 7,008,255 B1 | 3/2006 | Wang | |
| 7,025,618 B2 | 4/2006 | Fukuda | |
| 7,025,628 B2 | 4/2006 | LaMeres et al. | |
| 7,029,286 B2 | 4/2006 | Hall et al. | |
| 7,033,207 B2 | 4/2006 | Nimura | |
| 7,041,918 B1 | 5/2006 | Wu | |

(56) References Cited

U.S. PATENT DOCUMENTS

| | | |
|---|---|---|
| 7,056,134 B2 | 6/2006 | Martin et al. |
| 7,056,141 B2 | 6/2006 | Moffett et al. |
| 7,081,008 B2 | 7/2006 | Tan |
| 7,085,598 B2 | 8/2006 | Sato |
| 7,104,801 B1 | 9/2006 | Brodnick et al. |
| 7,110,804 B2 | 9/2006 | Baumer et al. |
| 7,117,590 B2 | 10/2006 | Koenig et al. |
| 7,118,411 B2 | 10/2006 | Huang et al. |
| 7,127,279 B2 | 10/2006 | Finneran et al. |
| 7,128,600 B2 | 10/2006 | Osypka |
| 7,134,908 B2 | 11/2006 | Wu |
| 7,137,839 B2 | 11/2006 | Dilliner et al. |
| 7,144,268 B2 | 12/2006 | Koenig et al. |
| 7,150,655 B2 | 12/2006 | Mastrototaro et al. |
| 7,160,136 B2 | 1/2007 | Zhang et al. |
| 7,169,107 B2 | 1/2007 | Jersey-Willuhn et al. |
| 7,179,111 B2 | 2/2007 | Van Der Mee et al. |
| 7,179,113 B2 | 2/2007 | Koenig et al. |
| 7,182,630 B1 | 2/2007 | Su |
| 7,184,820 B2 | 2/2007 | Jersey-Willuhn et al. |
| 7,189,097 B2 | 3/2007 | Benham |
| 7,197,357 B2 | 3/2007 | Istvan et al. |
| 7,198,502 B2 | 4/2007 | Koenig et al. |
| 7,201,599 B2 | 4/2007 | Holub |
| 7,207,825 B2 | 4/2007 | Le Gallic et al. |
| 7,236,825 B2 | 6/2007 | Wang |
| 7,252,542 B2 | 8/2007 | Chen |
| 7,252,556 B2 | 8/2007 | Anbo et al. |
| 7,258,565 B2 | 8/2007 | Huang |
| 7,258,566 B2 | 8/2007 | Koenig et al. |
| 7,264,510 B2 | 9/2007 | Koenig et al. |
| 7,270,568 B2 | 9/2007 | Osypka |
| 7,272,427 B2 | 9/2007 | Ristolainen |
| 7,272,428 B2 | 9/2007 | Hopman et al. |
| 7,275,951 B2 | 10/2007 | Shigeta et al. |
| 7,281,937 B2 | 10/2007 | Reed et al. |
| 7,287,998 B2 | 10/2007 | Masai |
| 7,303,430 B2 | 12/2007 | Butcher |
| 7,318,740 B1 | 1/2008 | Henry et al. |
| 7,319,895 B2 | 1/2008 | Klefstad-Sillonville et al. |
| 7,322,849 B2 | 1/2008 | Sutton |
| 7,322,857 B2 * | 1/2008 | Chen .......................... 439/638 |
| 7,329,139 B2 | 2/2008 | Benham |
| 7,333,850 B2 | 2/2008 | Marossero et al. |
| 7,347,710 B2 | 3/2008 | Ohtaka et al. |
| 7,347,826 B1 | 3/2008 | Karicherla et al. |
| 7,359,751 B1 | 4/2008 | Erickson et al. |
| 7,361,058 B1 | 4/2008 | Lien et al. |
| 7,371,102 B2 | 5/2008 | Sakamoto et al. |
| 7,373,196 B2 | 5/2008 | Ryu et al. |
| 7,374,448 B1 | 5/2008 | Jepsen et al. |
| 7,381,082 B2 | 6/2008 | Lai |
| 7,390,224 B2 | 6/2008 | Sodemann et al. |
| 7,396,246 B2 | 7/2008 | Okada et al. |
| 7,399,195 B2 | 7/2008 | Kim et al. |
| 7,401,946 B2 | 7/2008 | Laukhuf |
| 7,402,071 B2 | 7/2008 | Ohtaka et al. |
| 7,413,461 B2 | 8/2008 | Dawiedczyk et al. |
| 7,413,485 B2 | 8/2008 | Lappoehn |
| 7,416,440 B2 | 8/2008 | Homyk et al. |
| 7,422,437 B1 | 9/2008 | Lin et al. |
| 7,422,452 B2 | 9/2008 | Achtner et al. |
| 7,462,074 B1 | 12/2008 | Devlin et al. |
| 7,465,187 B1 * | 12/2008 | Wu .......................... 439/502 |
| 7,473,141 B2 | 1/2009 | Liao |
| 7,488,187 B2 | 2/2009 | Wolf |
| 7,494,383 B2 | 2/2009 | Cohen et al. |
| 7,497,738 B2 | 3/2009 | Kuo |
| 7,503,807 B2 | 3/2009 | Martin et al. |
| 7,556,535 B2 | 7/2009 | Liao |
| 7,581,992 B1 | 9/2009 | Liu et al. |
| 7,585,182 B2 | 9/2009 | Asante et al. |
| 7,591,673 B2 | 9/2009 | Chan et al. |
| 7,604,511 B1 | 10/2009 | Johnson |
| 7,618,377 B2 | 11/2009 | McAtamney et al. |
| 7,632,130 B2 | 12/2009 | Sami |
| 7,666,028 B2 | 2/2010 | Meleck |
| 2002/0133069 A1 | 9/2002 | Roberts |
| 2002/0138011 A1 | 9/2002 | Rantala |
| 2002/0188216 A1 | 12/2002 | Kayyali et al. |
| 2003/0068914 A1 | 4/2003 | Merry et al. |
| 2004/0073127 A1 | 4/2004 | Istvan et al. |
| 2004/0127802 A1 | 7/2004 | Istvan et al. |
| 2004/0176674 A1 | 9/2004 | Nazeri |
| 2005/0177052 A1 | 8/2005 | Istvan et al. |
| 2005/0203349 A1 | 9/2005 | Nanikashvili |
| 2006/0073728 A1 | 4/2006 | Zaiken et al. |
| 2007/0038057 A1 | 2/2007 | Nam et al. |
| 2007/0260133 A1 | 11/2007 | Meyer |
| 2008/0132106 A1 * | 6/2008 | Burnes et al. .............. 439/352 |

FOREIGN PATENT DOCUMENTS

| | | |
|---|---|---|
| EP | 0 766 946 | 4/1997 |
| EP | 0 766 946 A2 | 4/1997 |
| EP | 0 799 628 A2 | 10/1997 |
| EP | 1 050 269 A1 | 11/2000 |

OTHER PUBLICATIONS

European Search Report for EP 11 00 6002 dated Nov. 15, 2011.
European Search Report corresponding to European Application No. EP 07 25 3850, date of completion is Dec. 21, 2007; 2 pages.
European Search Report corresponding to European Application No. EP 07 25 4691, date of completion is Mar. 25, 2008; 2 pages.
European Search Report corresponding to European Application No. EP 07 25 1765, date of completion is Mar. 31, 2008; 2 pages.
European Search Report corresponding to European Application No. EP 08 16 4409, date of completion is Jan. 27, 2009; 2 pages.
Andreas Boos et al.; "A New Lightweight Fetal Telemetry System"; Dec. 1995; Hewlett-Packard Journal; pp. 82-93.

\* cited by examiner

ECG ADAPTER SYSTEM AND METHOD

CROSS REFERENCE TO RELATED APPLICATIONS

The present application claims priority from U.S. Provisional Patent Application No. 61/368,730 filed Jul. 29, 2010, the contents of which are incorporated herein by reference in its entirety.

BACKGROUND

1. Technical Field

The present disclosure relates to medical equipment. In particular, the present disclosure relates to an ECG lead system including one or more ECG lead sets, an adapter system, an extension cable and methods for coupling the one or more ECG lead sets with the adapter.

2. Background

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in and of themselves may also be inventions. Therefore, unless otherwise indicated herein, what is described in this section is not prior art to the description and claims in this application and is not admitted to be prior art by inclusion in this section.

Electrocardiograph (ECG) lead systems are used to obtain biopotential signals containing information indicative of the electrical activity associated with the heart and pulmonary system. To obtain biopotential signals, ECG electrodes are applied to the skin of a patient in various locations and coupled to an ECG device, e.g., an "ECG monitor" or "ECG telemetry." Placement of the electrodes is dependant on the information sought by the clinician.

The placement of the ECG electrodes on the patient has been established by medical protocols. The most common protocols require the placement of the electrodes in a 3-lead, a 5-lead or a 12-lead configuration. A 3-lead configuration requires the placement of three electrodes; one electrode adjacent each clavicle bone (RA, LA) on the upper chest and a third electrode adjacent the patient's lower left abdomen (LL). A 5-lead configuration requires the placement of the three electrodes in the 3-lead configuration with the addition of a fourth electrode adjacent the sternum (Va) and a fifth electrode on the patient's lower right abdomen (RL). A 12-lead configuration requires the placement of 10 electrodes on the patient's body. Four electrodes, which represent the patient's limbs, include the left arm electrode (LA lead), the right arm electrode (RA lead), the left leg electrode (LL lead), and the right leg electrode (RL lead). Six chest electrodes (V1-V6 leads) are placed on the patient's chest at various locations near the heart. Three standard limb leads are constructed from measurements between the right arm and left aim (Lead I), the right aim and the left leg (Lead H) and the left arm to left leg (Lead III).

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure relates to medical equipment. In particular, the present disclosure relates to an electrocardiograph (ECG) adapter including an adapter body having a first end and a second end, A monitor connector is positioned at the first end of the adapter body, the monitor connector adapted for coupling to an input of an ECG monitor. A first lead receptacle is positioned at the second end of the adapter body, the first lead receptacle configured to receive a first connector having a first pin configuration. A second lead receptacle is positioned at the second end of the adapter body, the second lead receptacle located adjacent the first lead receptacle and configured to receive a second connector having a second pin configuration different from the first pin configuration.

In accordance with one embodiment, the first lead receptacle includes a 2-pin configuration for receiving the first connector and the second lead receptacle includes a 6-pin configuration for receiving the second connector. In accordance with another embodiment, the first lead receptacle includes a single pin configuration.

In accordance with another embodiment, the second lead receptacle is adapted to connect to a second connector having a plurality of electrodes. The plurality of electrodes may include 5 electrodes. Additionally, a single electrode may be disposed at the proximal end of the first connector.

Moreover, the first connector is adapted to function when the second connector is disconnected. Alternatively, the second connector is adapted to function when the first connector is disconnected. Thus, the functionality of the first connector is independent of the functionality of the second connector. In another embodiment, the first connector and second connector are adapted to function when both the first connector and the second connector are connected.

In accordance with another embodiment, the first and second connectors are disposable connectors.

The present disclosure further relates to a method of coupling an electrocardiograph (ECG) monitor to one or more lead sets via an adapter. The method includes the steps of positioning a monitor connector at a first end of the adapter, the monitor connector adapted for coupling to an input of the ECG monitor; positioning a first lead receptacle at a second end of the adapter, the first lead receptacle configured to receive a first connector having a first pin configuration and positioning a second lead receptacle at the second end of the adapter, the second lead receptacle located adjacent the first lead receptacle and configured to receive a second connector having a second pin configuration different from the first pin configuration.

The present disclosure further relates to an electrocardiograph (ECG) lead set system including a first ECG lead set including a plurality of lead wires for coupling to a plurality of first electrodes and a second ECG lead set including a single wire for coupling to a second electrode. The system further includes a first plug connector coupled to one end of the first ECG lead set and a second plug connector coupled to one end of the second ECG lead set. The system also includes an adapter adapted for coupling the first and second plug connectors to an input of an ECG monitor. The adapter includes an adapter body having a first end and a second end and a monitor connector positioned at the first end of the adapter body, the monitor connector adapted for coupling to an input of the ECG monitor. The adapter further includes a first lead receptacle positioned at the second end of the adapter body, the first lead receptacle being configured to receive the first plug connector having a first pin configuration. The adapter also includes a second lead receptacle positioned at the second end of the adapter body, the second lead receptacle located adjacent the first lead receptacle and configured to receive the second plug connector having a second pin configuration different than the first pin configuration.

Other advantages, novel features and objects of the present disclosure will become apparent from the following detailed description of the present disclosure when considered in conjunction with the accompanying drawings, which are schematic and are not intended to be drawn to scale. In the figures, each identical, or substantially similar component is represented by a single numeral or notation. For purposed of clarity, not every component is labeled in every figure, nor is every component of each embodiment of the present disclosure shown where illustration is not necessary to allow those of ordinary skill in the art to understand the present disclosure.

DETAILED DESCRIPTION OF THE DRAWINGS

Various non-limiting embodiments of the present disclosure are described herein with reference to the drawings wherein.

The figures depict preferred embodiments of the present disclosure for purposes of illustration only. One skilled in the art will readily recognize from the following discussion that alternative embodiments of the structures and methods illustrated herein may be employed without departing from the principles of the present disclosure described herein.

DETAILED DESCRIPTION OF EMBODIMENTS,

Particular embodiments of the present disclosure are described hereinbelow with reference to the accompanying drawings. In the following description, well-known functions or constructions are not described in detail to avoid obscuring the present disclosure in unnecessary detail, As used herein and as is traditional, the term "distal" refers to the portion which is furthest from the user/clinician and the term "proximal" refers to the portion that is closest to the user/clinician. In addition, terms such as "above," "below," "forward," "rearward," etc. refer to the orientation of the figures or the direction of components and are simply used for convenience of description.

In the following detailed description, example embodiments disclosing specific details are set forth in order to provide an understanding of the present disclosure. The example embodiments are set forth for purposes of explanation and not limitation. Those of ordinary skill in the art will understand that various changes in form and details may be made to the example embodiments without departing from the scope of the present disclosure. Moreover, descriptions of well-known devices, methods, systems, and protocols may be omitted so as to not obscure the description of the example embodiments. Nonetheless, such devices, methods, systems and protocols that are within the purview of those of ordinary skill in the art are contemplated by the example embodiments.

Embodiments will be described below while referencing the accompanying figures. The accompanying figures are merely examples and are not intended to limit the scope of the present disclosure.

One aspect of the present disclosure provides an ECG electrode system which allows a patient to be monitored by a first electrode lead set having a first configuration which may remain with the patient as monitoring requirements change, and in particular, as additional information is sought. The configuration of the electrodes is determined by the information sought. Electrodes, after placement on the patient, connect to an ECG device by an ECG lead set. One end of the ECG lead set, closest to the patient, connects to each electrode (alternatively, the electrodes may be integrated into the distal end of the ECG lead set) and receives biopotential signals from the body. The other end of the ECG lead set connects to the ECG input connector and supplies the biopotential signals received from the body to the ECG device. Conventional lead sets are prearranged in a particular configuration to obtain the desired information. For example, lead sets are typically available for standard electrode configurations, such as a 3 lead, 5 lead, 6 lead, 10 lead or 12 lead.

ECG devices and ECG lead sets are also typically manufactured and sold by various companies. Although protocols have been established for the placement ECG electrodes, the various manufacturers typically use product specific connectors and wiring configurations. A patient may also be initially monitored with one lead configuration, but require a different lead configuration upon extended monitoring.

Often, one or more lead sets may be used for a single patient as monitoring requirements change during patient evaluation and treatment. In many instances, a patient may require one type of ECG lead system while in, for example, the emergency room (ER), the operating room (OR), the post-anesthesia care unit (PACU), the intensive care unit (ICU) and/or the critical care unit (CCU); and may require a second or different type ECG lead system while on, for example, a telemetry floor. For example, a patient may require a relatively longer ECG lead set in order to connect to an ECG monitor while the patient is in the ER, the OR, the PACU, the ICU and/or the CCU; and a relatively shorter ECG lead set in order to connect to ECG telemetry while the patient is on a telemetry floor. In particular, a patient may be initially monitored with a 5 lead configuration and subsequently switched to a 6 lead configuration. Specifically, the 5-lead configuration requires the placement of the five electrodes RA, LA, LL, Va, and RL, while the 6-lead configuration includes a Vb electrode in addition to the previous five electrodes.

According to one embodiment of the present disclosure, a system that enables an end user to use a single ECG lead set across various ECG device platforms and to accommodate the use of the ECG lead set with either an ECG monitor and/or ECG telemetry as desired is provided.

Figure 1:
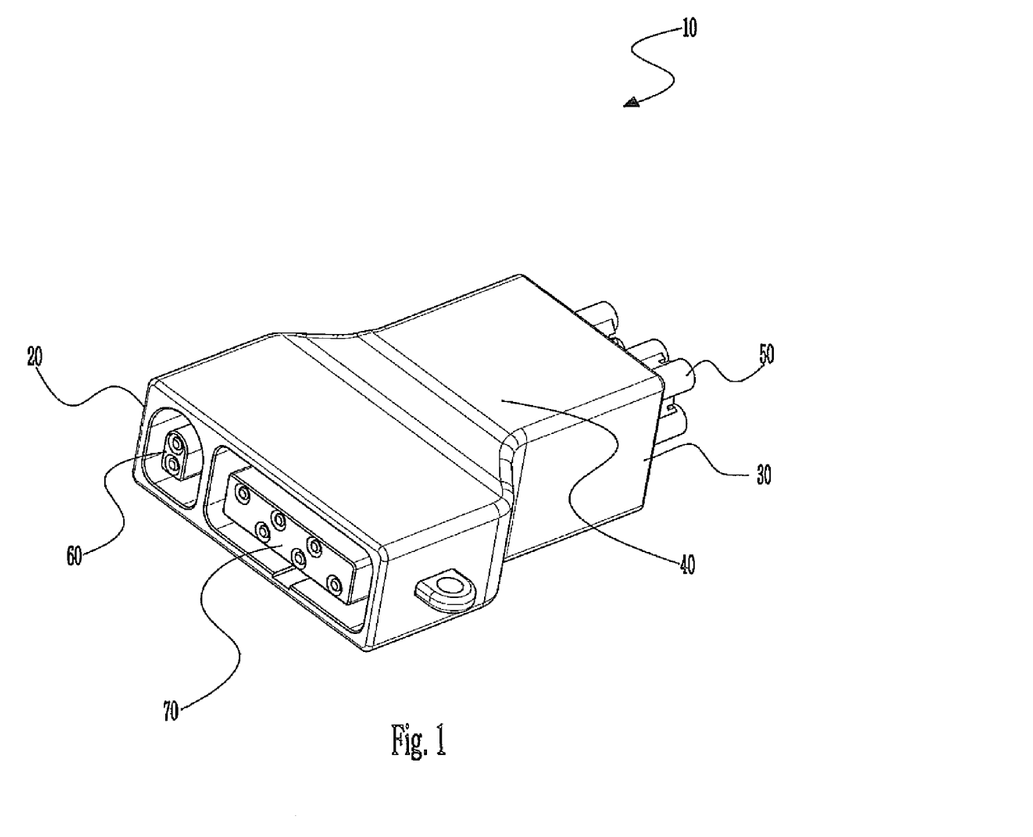
FIG. 1 is a perspective, front view of an adapter at a first angle, according to the present disclosure.
Figure 2:
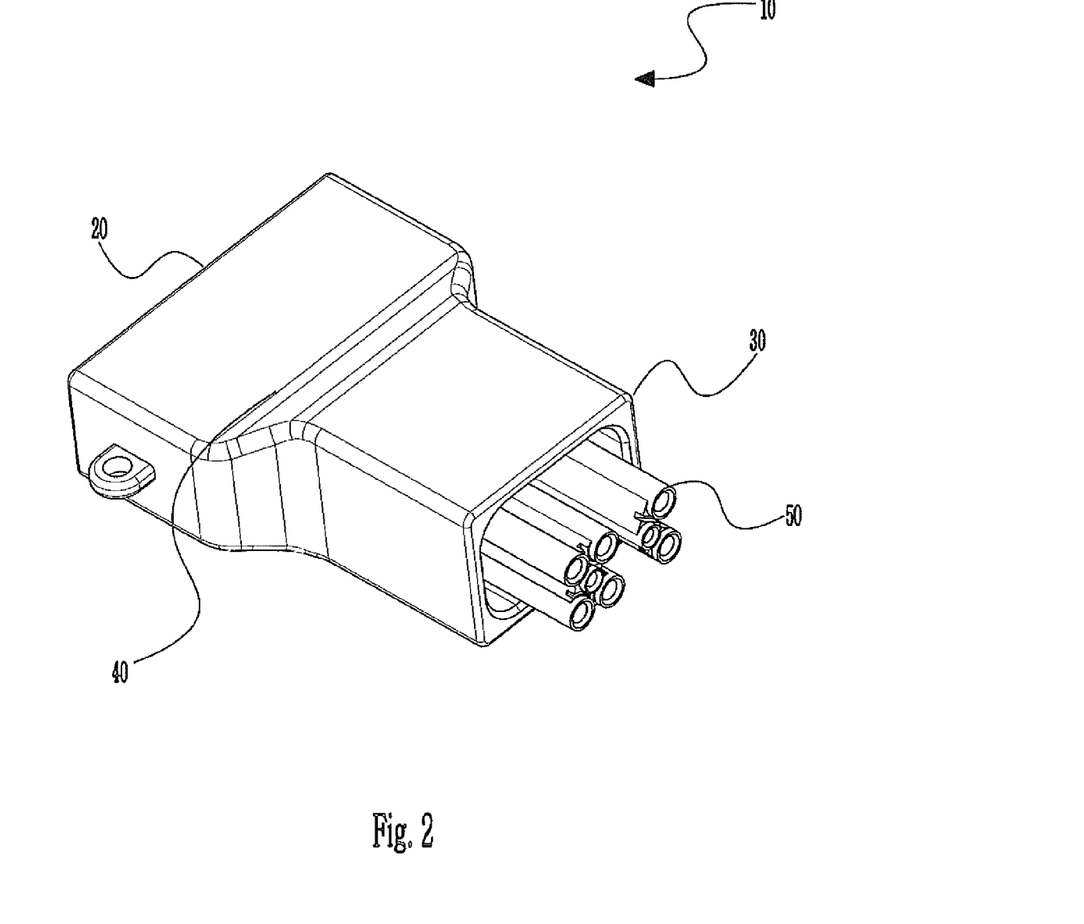
FIG. 2 is a perspective, rear view of the adapter, according to the present disclosure.
Figure 3:
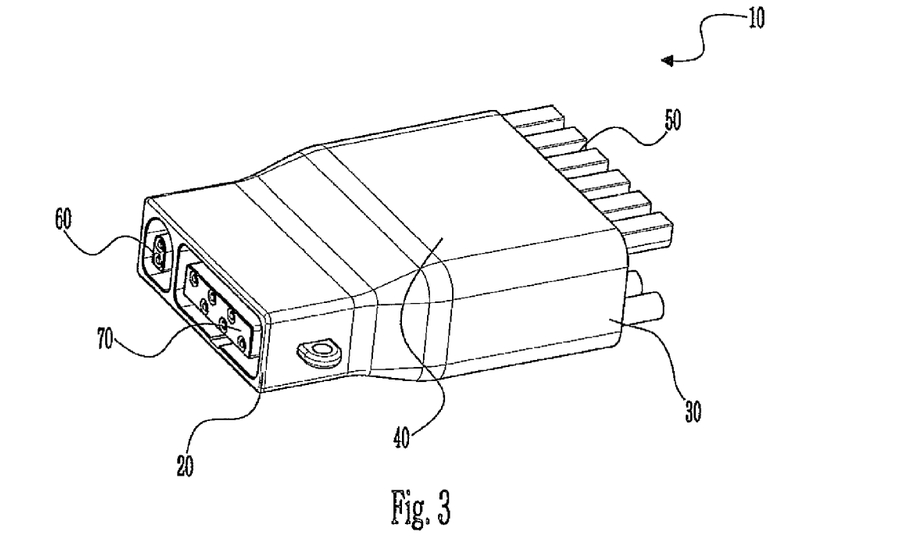
FIG. 3 is a perspective, front view of an adapter at a second angle, according to the present disclosure.

Referring to FIGS. 1-3, an adapter 10, in accordance with the principles of the present disclosure, is illustrated. Adapter 10 includes an adapter body 40 having a first end 20 and a second end 30. First end 20 may be a front end of adapter body 40, whereas second end 30 may be a rear end of adapter body 40. Adapter 10 also includes a plurality of plugs 50 at second end 30 of adapter body 40 and at least two pin configurations 60, 70 at first end 20 of adapter body 40. Plugs 50 at second end 30 may have any conventional configuration, such as cylindrical, rectangular or any regular or irregular cross sectional area suitable for a particular purpose.

In the embodiment shown in FIGS. 1-3, a first pin configuration 60 includes 2-pins, whereas second pin configuration 70 includes 6-pins. It is understood that pin configurations 60, 70 may vary depending on the desired application and the specific lead set or lead sets to be used. For example, pin configuration 60 may include only a single pin used in an unshielded configuration of a single electrode lead set. Pin configurations 60, 70 are depicted as female connectors. However, one skilled in the art may contemplate using male connectors at first end 20 of adapter body 40. One skilled in the art may also contemplate using a plurality of different pin configurations.

The plurality of plugs 50 may be a five (5) plug pin male socket connector (each plug having a pair of sockets, wherein one plug corresponds to one ECG lead and the corresponding plug carries the shield) similar to those specified by ANSI/AAMI EC53 for shielded leadwire to trunk cable interconnections. The plurality of plugs 50 may be referred to as monitor plugs. Monitor plugs 50 are configured for coupling to the lead set input connector of ECG floor monitor 710 (see FIG. 7). Monitor plugs 50 may include a plurality of male contact pins for establishing an electrical connection between ECG floor monitor 710 and device connectors 110, 120 (see FIG. 4).

Thus, as seen in FIGS. 1-3, adapter 10 generally includes adapter body 40, at least two input receptacles 60, 70 disposed on first end 20 of adapter body 40, and monitor plugs 50 disposed on second end 30 of adapter body 40. First input receptacle 60 is configured to be located adjacent to or in proximity to second input receptacle 70. Each of the input receptacles 60, 70 is configured to electrically couple with a device connector 110, 120 (see FIG. 4). Each of the input receptacles 60, 70 includes a plurality of electrical contact receptacles for connection with, for example, male pin contacts of the device connectors 110, 120 (see FIG. 4).

Figure 4:
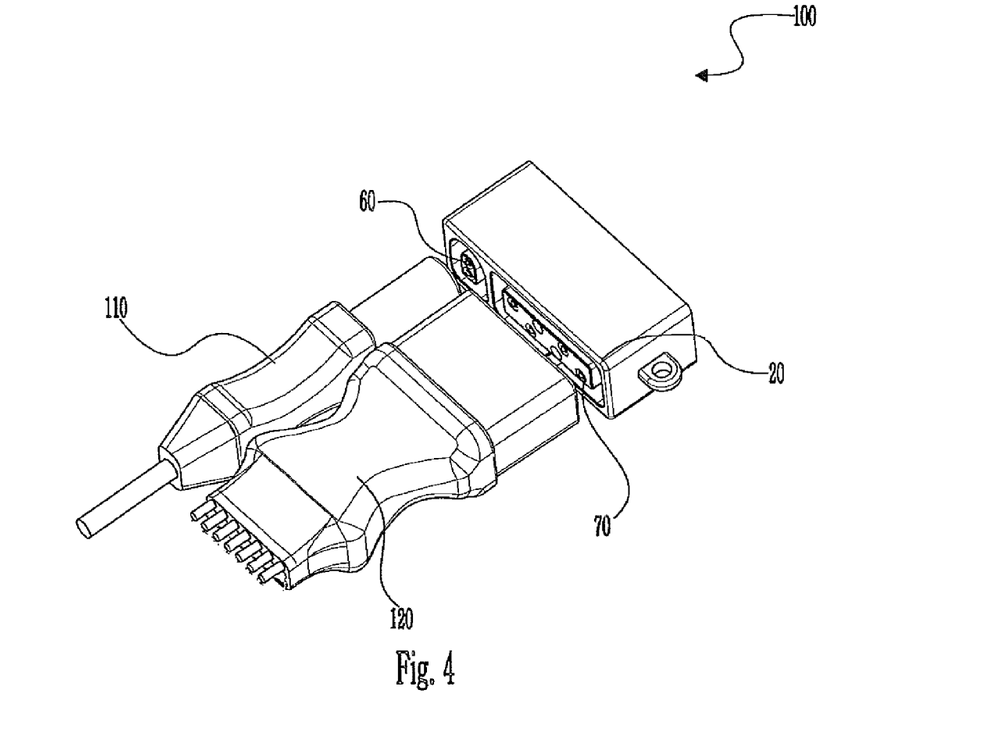
FIG. 4 is a perspective view of a portion of the adapter having a first and a second receptacle for receiving first and second plug connectors, respectively, according to the present disclosure.

Referring to FIG. 4, a perspective view 100 of a portion of adapter 10 having first and second receptacles 60, 70 for receiving first and second plug connectors 110, 120 is shown. First plug connector 110 is connected to the 2-pin input receptacle 60, whereas second plug connector 120 is connected to the 6-pin input receptacle 70 (see FIGS. 1-3). Thus, in accordance with the present disclosure, device connectors 110, 120 (or plug connectors) are configured and dimensioned to mate and electrically connect with input receptacles 60, 70 of adapter 10.

In particular, first input receptacle 60 is configured to receive first device connector 110 having a first pin configuration and second input receptacle 70 is configured to receive second device connector 120 having a second pin configuration, the first and second pin configurations being different with respect to each other. Additionally, first input receptacle 60 is constructed and arranged to receive a single electrode assembly, whereas second input receptacle 70 is constructed and arranged to receive a 5-lead electrode assembly. As a result, by adding or removing a specific lead set, the lead set assembly may be instantly transformed/modified/altered from a 5-lead set to a 6-lead set, and from a 6-lead set to a 5-lead set, without replacing an entire 5-lead set with an entire 6-lead set and without replacing an entire 6-lead set with a 5-lead set. Moreover, switching between a 5-lead and a 6-lead set may be accomplished without interrupting patient monitoring of biopotential signals.

Figure 5A:
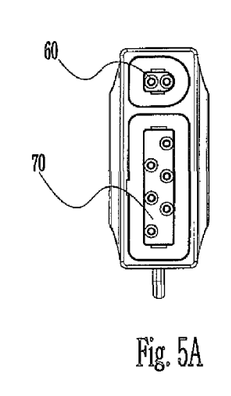
FIGS. 5A-5E are top, bottom and side views of the adapter of FIG. 1, according to the present disclosure.
Figure 5B:
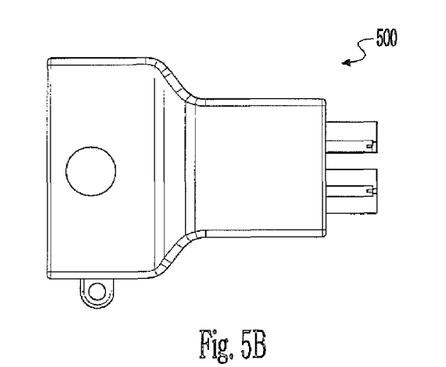
Figure 5C:
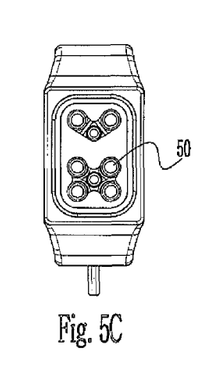
Figure 5D:
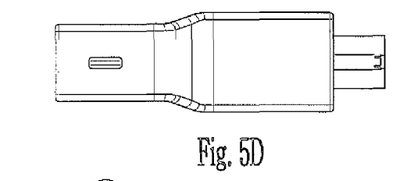
Figure 5E:
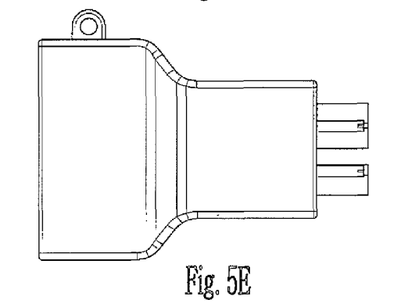

Referring to FIGS. 5A-5E, top, bottom and side views 500 of adapter 10 are depicted. For example, FIG. 5A depicts a front view of the 2-pin and 6-pin input receptacles 60, 70 (as described above). For example, FIG. 5C depicts a front view of plurality of plugs 50 (as described above). With reference to FIGS. 1-5E, when first input receptacle 60 is disconnected from adapter 10, second input receptacle 70 continues to function. Alternatively, when second input receptacle 70 is disconnected from adapter 10, first input receptacle 60 continues to function. Thus, the functionality of first input receptacle 60 is independent of the functionality of second input receptacle 70. Therefore, the 5-lead disposable lead wire set may be used as a 6-lead telemetry lead set, so that the clinician may require only one lead set for a patient that experiences 3/5 lead monitoring followed by a 6-lead telemetry monitoring. By requiring only one lead set instead of two lead sets, a clinician may perform his/her job more efficiently and use less lead sets. As a result, the lead set may be conveniently and instantly transformed or altered from a 5-lead set to a 6-lead set. Alternatively, the lead set may be conveniently and instantly transformed or altered from a 6-lead set to a 5 lead set.

Figure 7:
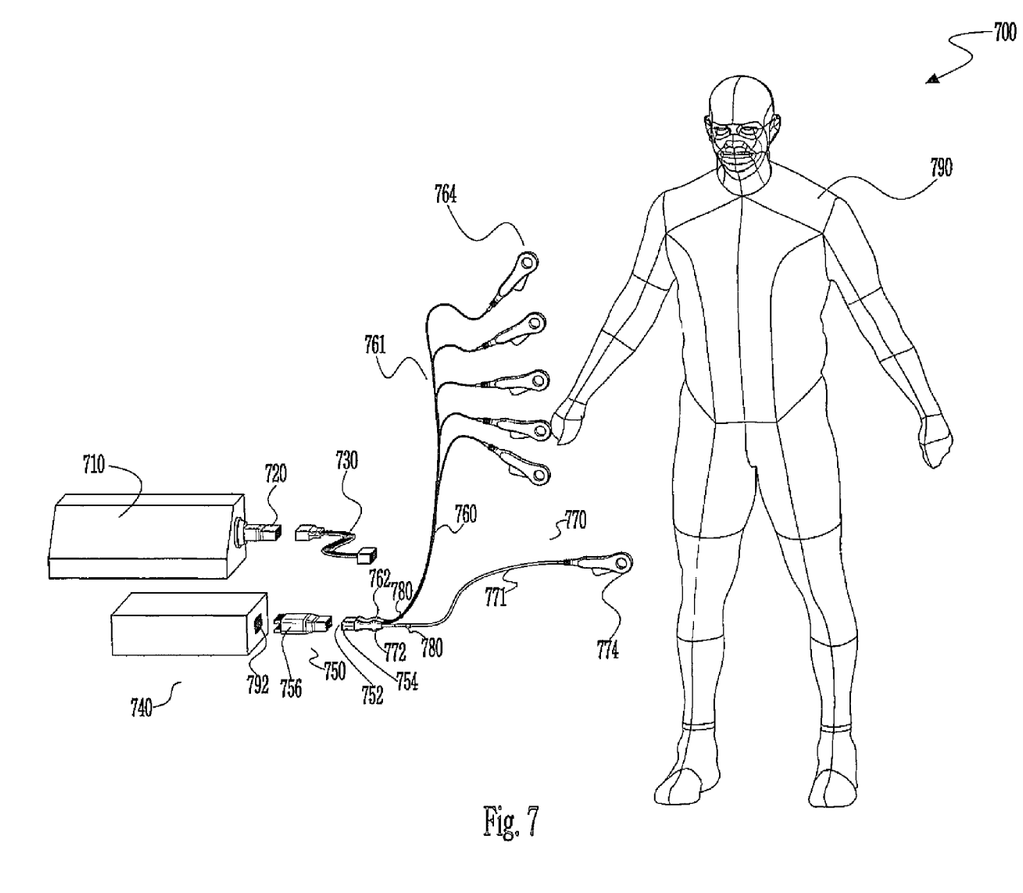
FIG. 7 is a schematic diagram of an ECG lead set system, according to the present disclosure.

Referring to FIG. 7, ECG lead system 700, in accordance with the present disclosure, is used in connection with an ECG device or monitor, in the form or ECG floor monitor 710 or ECG telemetry monitor/adapter 740. ECG floor monitor 710 includes at least one lead set input connector 720 configured to connect with at least one ECG lead set assembly 730. ECG lead system 700 includes adapter 750. ECG monitor 710 is configured to receive biopotential signals containing information indicative of the electrical activity associated with the heart and pulmonary system and to display the information of a user display (not shown).

Of course, as contemplated by one skilled in the art, depending on the type of ECG floor monitor 710 or ECG telemetry monitor 740, and depending on whether a 3-lead, a 5-lead or a 12-lead electrode set assembly 760, 770 is used, and depending on whether one or more ECG lead set assemblies are used, any type of adapter may be utilized based on the desired medical application. For simplicity purposes, the example embodiments of the present disclosure refer to a 5-lead electrode set and a 1-lead electrode set connected to a 6-pin input receptacle 70 and a 2-pin input receptacle 60, respectively.

Figure 6A:
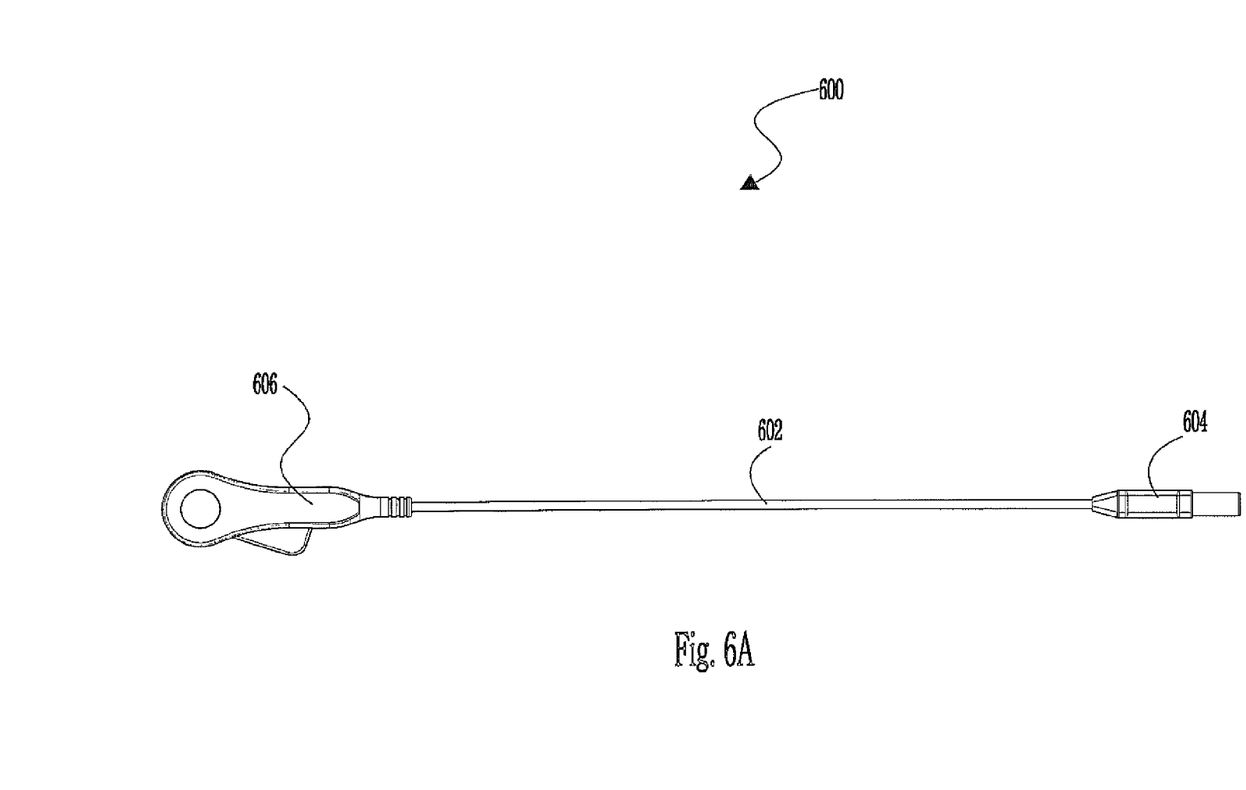
FIG. 6A is a perspective view of a 2-pin configuration lead connector, according to the present disclosure.
Figure 6B:
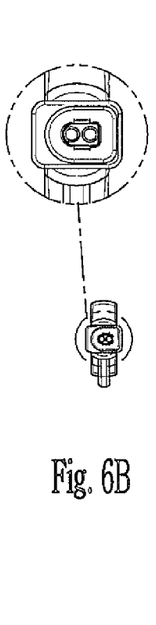
FIG. 6B is an end view of the connector of FIG. 6A.

As seen in FIGS. 6A-6B, ECG lead set assembly 600 for the 2-pin input receptacle 60 includes lead set cable 602, device connector 604 at one end of lead set cable 602 and at least one electrode connector 606. Lead set cable 602 includes a plurality of encased and insulated lead wires (not shown) disposed in side-by-side relation. Insulated lead wires may be EMI/RF shielded. Lead set cable 602 may be in the form of a ribbon cable configured for transmitting electrical signals. Each lead wire may be independently separable from an adjacent lead wire to facilitate placement of a respective electrode connector 606 at a predetermined body location, to thereby permit customization of ECG lead set assembly 600 for each subject. Lead wires may be attached via their insulated covers and, may be separable along respective lines of juncture of the insulated covers of adjacent lead wires. Individual lead wires of lead set cable 602 may be varied in length to permit placement of an individual electrode connector 606 at a target site, e.g., across the chest or abdomen, to permit collection or delivery of biomedical signals at these locations. Similarly, it is contemplated that each electrode assembly of 6-pin input receptacle 70 is the same or equivalent to the electrode assembly of 2-pin input receptacle 60.

With continued reference to FIG. 7, ECG lead system 700 includes ECG telemetry adapter 740 configured and adapted to interconnect at least one ECG lead set assembly 600 (see FIG. 6) to ECG telemetry monitor 740. ECG telemetry adapter 740 includes an adapter body, at least one input receptacle 742 disposed on one side of adapter body, and a telemetry plug (not shown) disposed on another side of adapter body. Each input receptacle 742 is configured to electrically mate with adapter 750. In particular, input receptacle 742 is in the form of an AAMI type plug, and telemetry plug is in the form of a GE 5 prong, 10-pin telemetry plug that is configured and adapted to mate with and electrically connect to ECG telemetry monitor 740.

Thus, ECG adapter system 700 includes adapter 750 and one or more ECG lead sets 760, 770. Each ECG lead set 760, 770 includes a plurality of lead wires 761, 771 at least partially surrounded by sheath 780. Sheath 780 may protect lead wires 761, 771 from physical damage or may shield lead wires 761, 771 from electrical interference. Sheath 780 may vary in length between about 2 feet to about 10 feet. At least a portion of lead wires 761, 771 extends distally from sheath 780 a distance "d," between about 2 to about 40 inches. Sheath 780 may be integrated into ECG lead sets 760, 770 or may be formed from a suitable tubular material and coupled to ECG lead sets 760, 770. The distal end of lead wires 761, 771 may connect to one or more electrodes 764, 774. Alternatively, lead wires 761, 771 may be integrated into electrodes 764, 774. One or more electrodes 764, 774 may be coupled to the distal end of each individual lead wire 761, 771 or electrodes 764, 774 may be formed from individual lead wires 761, 771.

Alternatively, electrode connectors (not shown) may be positioned between the electrodes 764, 774 and the distal end of lead wires 761, 771. Such electrode connectors may be attached to, or formed on, the distal end of lead wires 761, 771. The electrode connectors may be snap connectors, locking slot connectors and/or keyhole connectors. One skilled in the art may contemplate using a plurality of different connection mechanism and/or configurations.

In operation, when patient 790 is in, for example, the emergency room (ER), the operating room (OR), the post-anesthesia care unit (PACU), the intensive care unit (ICU) and/or the critical care unit (CCU), patient 790 is typically connected to ECG floor monitor 710. In particular, patient 790 may be connected to a 5-lead ECG lead set 760 via electrodes 764. ECG lead set 760 is mated with and electrically connected to ECG lead wires 761 and ECG lead wires 761 are mated with and electrically connected to adapter 720. A lead extension 730 may be disposed between lead set 760 and adapter 720.

In continued operation, following patient's 790 stay in the emergency room (ER), the operating room (OR), the post-anesthesia care unit (PACU), the intensive care unit (ICU) and/or the critical care unit (CCU), if and/or when patient 790 is transferred to a telemetry floor for monitoring, the need for one of the ECG lead extensions may no longer be necessary if patient 790 is to be connected to ECG telemetry monitor 740. Patent 790 may also now require another ECG lead in addition to the 5-lead system already connected to the patient. Accordingly, in one embodiment, the 5-lead set 760 is disconnected from adapter 770 or lead extension 730.

The 5-lead ECG set currently attached to the patient may then also be connected to adapter 750. In addition, a single ECG lead 770 may also be connected to adapter 750 and to the patient. Adapter 750 is mated with and electrically connected to ECG telemetry box 740. Adapter 750 includes first input receptacle 752 and second input receptacle 754 at a first end. First input receptacle 752 is configured to receive first connector 762 of ECG lead set 760, whereas second input receptacle 754 is configured to receive second connector 772 of ECG lead set 770. Adapter 750 also includes plurality of plugs 756 at a second end. As such, the 5-lead ECG set which was first used with a patient may remain with the patient as the patient is switched from a 5-lead configuration to a 6 lead configuration, and vice versa, Similarly, at least one ECG lead extension (e.g., lead set 770) may be removed and the other ECG lead set (e.g., lead set 760) mated with and electrically connected to ECG telemetry adapter 740 via input receptacle 742. Thus, the need for at least one of the ECG lead extensions/lead sets is no longer necessary since patient 790 transferred from lead wire monitoring to telemetry wiring, or vice versa.

In this manner, the same ECG lead sets 760, 770 may be used for the emergency room (ER), the operating room (OR), the post-anesthesia care unit (PACU), the intensive care unit (ICU) and/or the critical care unit (CCU), and for the telemetry floor. Thus, when first lead set 760 is disconnected from adapter 750, second lead set 770 continues to function. Alternatively, when second lead set 770 is disconnected from adapter 750, first lead set 760 continues to function. Thus, the functionality of the first lead set 760 is independent of the functionality of the second lead set 770. Therefore, the 5-lead disposable lead wire set may be used as a 6-lead telemetry lead set, so that the clinician may require only one lead set for a patient that experiences 3/5 lead monitoring followed by a 6-lead telemetry monitoring. By requiring only one lead set instead of two lead sets, a clinician may perform his/her job more efficiently and use less lead sets. As a result, the lead set may be instantly transformed/modified from a 5-lead set to a 6-lead set, and vice versa.

Figure 8:
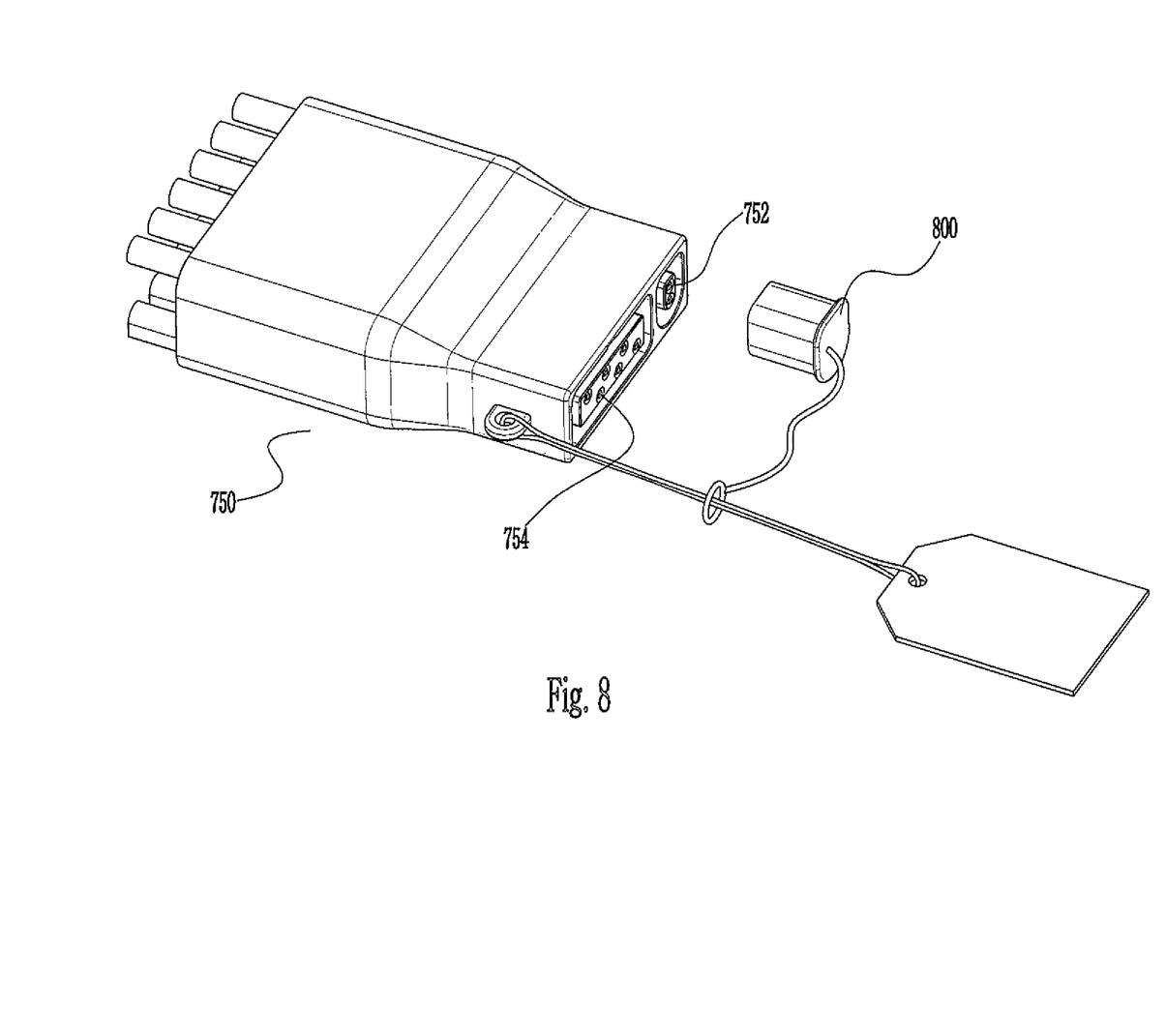
FIG. 8 is a perspective view of a plug protector, according to another aspect of the present disclosure.

In one embodiment of the present disclosure, adapter 750 is constructed and arranged to operate when either first input receptacle 752 or second input receptacle 754 or both input receptacles 752 and 754 are connected to first connector 762 and second connector 772, respectively, In one embodiment, adapter 750 may also include a plug cover to protect either input receptacles 752, 754 when not in use. For example and as shown in FIG. 8, adapter 750 may also comprise plug cover 800 which connects to second input receptacle when the single lead set 770 is not in use. Plug protector 800 may comprise a first end connected to adapter 750 and a second end constructed and arranged to mate with second input receptacle 754, thereby preventing contamination of the receptacle which could interfere with the electrical connection with the single ECG lead 770 if later connected to adapter 750.

Further, although aspects of the present disclosure have been described herein in the context of several particular implementations in particular environments for particular purposes, those of ordinary skill in the art will recognize that its usefulness may not be limited thereto and that the present disclosure may be beneficially implemented in any number of environments for any number of purposes.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrocardiograph (ECG) lead set system comprising:
   a first ECG lead set comprising exactly one wire for coupling to a first electrode;
   a second ECG lead set including a plurality of lead wires for coupling to a plurality of second electrodes;
   a first plug connector coupled, at one end of the first ECG lead set, to only the exactly one wire;
   a second plug connector coupled to one end of the second ECG lead set; and
   an adapter adapted for coupling the first and second plug connectors to an input of an ECG monitor, the adapter including:
      an adapter body having a first end and a second end;
      a monitor connector positioned at the first end of the adapter body, the monitor connector adapted for coupling to an input of the ECG monitor;
      a first lead receptacle positioned at the second end of the adapter body, the first lead receptacle configured to receive the first plug connector having a first pin configuration; and
      a second lead receptacle positioned at the second end of the adapter body, the second lead receptacle located adjacent the first lead receptacle and configured to receive the second plug connector having a second pin configuration different from the first pin configuration.

2. The system according to claim 1, wherein the first lead receptacle includes a 2-pin configuration for receiving the first plug connector.

3. The system according to claim 1, wherein the second lead receptacle includes a 6-pin configuration for receiving the second plug connector.

4. The system according to claim 1, wherein the second lead receptacle is adapted to connect to a second connector having a plurality of electrodes.

5. The system according to claim 4, wherein the second plug connector is adapted to couple with a second plug connector having 5 electrodes.

6. The system according to claim 1, wherein the single electrode is disposed at the proximal end of the first plug connector.

7. The system according to claim 1, wherein the first plug connector is adapted to function if the second plug connector is disconnected from the adapter.

8. The system according to claim 1, wherein the second plug connector is adapted to function when the first plug connector is disconnected from the adapter.

9. The system according to claim 1, wherein the first plug connector and the second plug connector are adapted to function if the first plug connector and the second plug connector are connected to the adapter.

10. The system according to claim 1, wherein the functionality of the first plug connector is independent of the functionality of the second plug connector.

11. The system according to claim 1, wherein the first and second plug connectors are disposable connectors.

12. The system according to claim 1, further comprising a plug protector connected to the adapter.

* * * * *